United States Patent [19]

Hanson

[11] 4,270,528
[45] Jun. 2, 1981

[54] FINGER RING SPLINT

[76] Inventor: Catherine F. Hanson, 3199 Claudia Dr., Concord, Calif. 94519

[21] Appl. No.: 89,254

[22] Filed: Oct. 29, 1979

[51] Int. Cl.³ .............................................. A61F 5/04
[52] U.S. Cl. .................................... 128/87 A; 128/77
[58] Field of Search .......................... 128/87 A, 77, 83

[56] References Cited

U.S. PATENT DOCUMENTS 3,170,460   2/1965   Stilson .................................... 128/77

Primary Examiner—John D. Yasko
Attorney, Agent, or Firm—Harris Zimmerman; Howard Cohen

[57] ABSTRACT

A finger ring splint for preventing hyperextension of a finger joint includes a generally circular portion which is secured about the finger adjacent to the joint and disposed between the joint and the hand. A second elliptical ring portion is secured about the same finger forwardly of the same joint. The circular ring portion is disposed in a plane perpendicular to the axis of the finger, while the elliptical portion is disposed in a plane which is oblique with respect to the axis of the finger. Both ring portions are joined together at an apex which is adjacent to the palm of the hand. The ring structure does not interfere with normal flexure of the joint, but prevents hyperextension of the joint.

6 Claims, 5 Drawing Figures

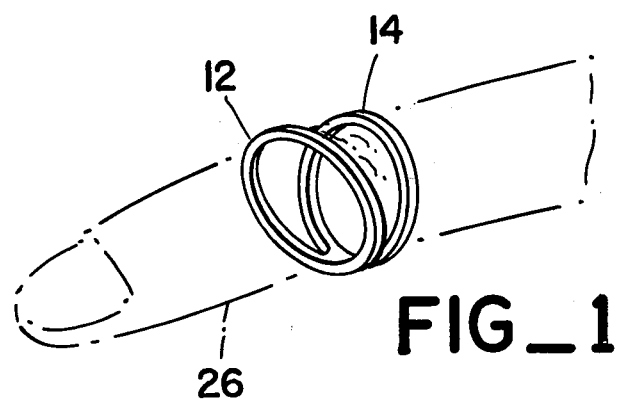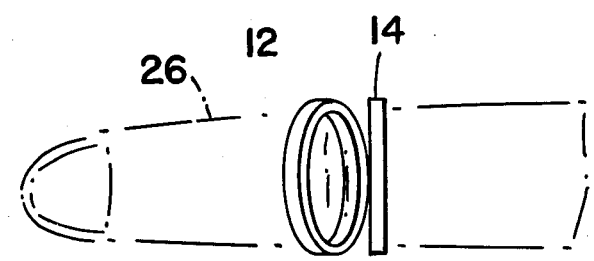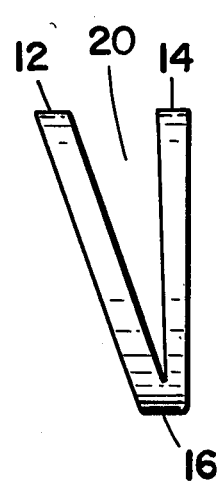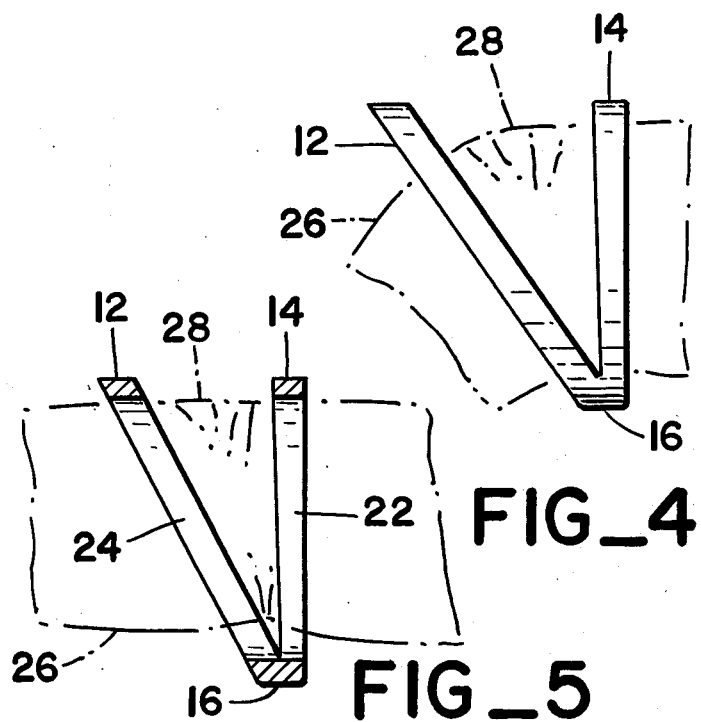

FINGER RING SPLINT

BACKGROUND OF THE INVENTION

The following U.S. Pat. Nos. represent the closest known prior art: D 131,948, 2,394,794, 3,091,455, 3,533,405, 3,994,493.

Arthritic and rheumatic conditions are associated with deterioration of the bone structure of the body, and this deterioration can be extremely unpleasant when localized in the bones of the hand. The phalangeal joints of the hand may become difficult to flex, exhibiting stiffness and pain upon flexure.

Another condition of the hand arising from arthritic or rheumatic disease is the tendency of the finger joints to hyperextend. When a finger joint is hyperextended, the abductor muscles in the finger are often positioned in such a way that they cannot flex the finger joint to restore the finger to a normal disposition. In this circumstance, the finger joint is stuck in the hyperextended position, and must be restored to a normal position by manipulation or the like.

There are known in the prior art many types of finger splints and support devices to increase the strength of finger joints. Interestingly enough, many of these devices are designed to strengthen the finger joints for athletic endeavors, such as bowling. Generally speaking, the prior art devices include some sort of flexible tube which is received about the finger joint to increase the amount of force required to flex the joint. The tube may be reinforced with ring members, semi-rigid longitudinally extending members, and the like.

These prior art constructions are effective in strengthening and rigidifying finger joints, but they also suffer from a common drawback; that is, they all significantly limit flexure of the finger joint which is being supported. Although in a sport such as bowling the limitations on the degree of flexure of the finger joint imposed by the reinforcing member are insignificant, quite the opposite is true in the case of finger joints which are damaged by arthritis or other bone diseases. Indeed, any reinforcing device for finger joints which reduces their flexibility while preventing hyperextension of the joint is merely trading one problem for another. It is believed that there is no device in the prior art designed for this sort of medical problem in which it is desirable to prevent hyperextension of a joint while at the same time permitting free flexure of the joint.

SUMMARY OF THE PRESENT INVENTION

The present invention generally comprises a ring type finger splint which is particularly adapted to be secured about a finger joint to prevent hyperextension thereof. A salient feature of the splint is that it provides no interference with the normal flexure of the finger joint.

The splint includes a pair of ring members joined at an apex and extending in a V-configuration therefrom. The ring members are adapted to receive a portion of a finger therethrough with the proximal interphylangeal joint of the finger disposed between the two ring members. One of the rings in generally circular in configuration, and is received about the finger adjacent to the proximal portion of the finger joint. The other ring member is generally elliptical in configuration, and is positioned forwardly of the finger joint. The apex of the splint is disposed directly adjacent to the finger joint, at the side of the joint toward which the finger joint is typically flexed. The material which forms the ring splint is adjustable so that the V-configuration of the two ring members may be modified to suit individual finger requirements.

It may be appreciated that neither abduction nor flexion of the joint is interefered with in any way, since the span between the two ring members freely receives the joint portion of the finger and provides no interference therewith. However, hyperextension of the joint is completely blocked by the ring splint, since the elliptical ring limits extension of the distal phalanges to 180° or less, depending on preferred adjustment. The splint is simple, lightweight, and as unobtrusive as any jewelry designed for the fingers.

A BRIEF DESCRIPTION OF THE DRAWING

FIG. 1 is a perspective view of the ring splint of the present invention.

FIG. 2 is a top view of the ring splint of the present invention.

FIG. 3 is a side elevation of the present invention, shown disposed in a narrow V-configuration.

FIG. 4 is a side elevation of the present invention, shown in a wide V-configuration.

FIG. 5 is a cross-sectional side elevation of the ring splint of the present invention.

DESCRIPTION OF THE PREFERRED EMBODIMENT

The present invention generally is characterized as a finger splint which is designed to prevent hyperextension of a finger joint while providing little or no interference with normal flexion of the finger joint. With reference to the accompanying figures, the splint of the present invention includes a pair of ring members 12 and 14 which are disposed in non-parallel adjacent fashion. The ring members are joined at a common apex 16, and are integrally formed from a single piece of metal, plastic, or the like. The ring members 12 and 14 are thus disposed in a V-configuration, with the apex 16 comprising the apex of the V-configuration.

The ring member 14 is generally circular in configuration, while the ring member 12 is generally elliptical in configuration. The distal portions of the ring members 12 and 14 define therebetween medial gap 20 in which the joint portion of a finger is to be received. It should be noted that in the preferred embodiment of the present invention, the rings are formed of a moderately rigid material which is capable of some adjustment. This quality of the preferred material permits the ring members 12 and 14 to be adjusted slightly about the apex 16 to vary selectively the size of the medial gap 20 in accordance with the size of the joint to be received therein.

The splint of the present invention is used by first inserting the tip of the finger through the opening 22 in the ring member 14, and thence through the opening 24 of the ring member 12. The splint is then slid onto the finger so that the finger joint is received within the medial gap 20 of the splint, as shown in FIGS. 1 and 2. In this disposition, the circular ring member 14 is disposed directly adjacent to the proximal side of the finger joint. The elliptical ring member 12 is disposed directly adjacent to the distal portion of the same finger joint. The apex 16 of the splint is located substantially at the midline of the finger joint and adjacent to the side of the finger joint toward which the joint is flexed; i.e., adjacent to the palm of the hand.

As shown in phantom line in FIG. 5, the finger when adducted to a substantially axial configuration extends through the generally colinear portions of the ring members 12 and 14. It is apparent from the illustration of FIG. 5 that any extension of the finger joint 28 beyond normal extension will cause the distal finger portion 26 to impinge on the distal portion of the ring 12 and thus be limited in movement. As a result, the distal portion of the ring 12 prevents hyperextension of the joint 28 by limiting the movement of the member 26 at full extension. Thus those individuals suffering from conditions which result in inadvertent hyperextension of the finger joint may be relieved of this awkward, difficult, and sometimes painful condition.

At the same time the splint of the present invention provides no impediment to normal flexion of the same finger joint. As shown in FIG. 4, the finger joint may flex freely within the confines of the splint of the present invention. As flexion of the joint increases, the crown of the joint 28 is freely disposed within the medial gap 20, and complete flexion of the joint may be performed.

It may be appreciated that the ring member 14 is secured more snugly about its respective finger portion that the ring member 12. Thus the ring member 14 acts to anchor the splint in position so that the distal portions of the ring members 12 and 14 straddle the joint while the apex 16 is maintained substantially at the midline of the same joint. The elliptical configuration of the ring member 12 provides the freedom of movement for the distal portion 26 so that complete flexion of the joint may be performed.

I claim:

1. A finger splint for preventing hyperextension of a finger joint while permitting free flexion of the finger joint, comprising a first ring member adapted to encircle the finger and disposed rearwardly of the finger joint, said first ring member being generally circular and adapted to be closely fitted about the finger, a second ring member adapted to encircle the finger forwardly of the finger joint and directly adjacent thereto, said ring members extending from a common apex, the portion of said second ring member distal from said apex adapted to impinge on the forward portion of said joint during full extension thereof to prevent hyperextension thereof.

2. The finger splint of claim 1, wherein said first ring member is fixed in a plane perpendicular to the axis of the finger portion it encircles.

3. The finger splint of claim 1, wherein said second ring member is generally elliptical in configuration.

4. The finger splint of claim 1, wherein said ring members diverge from said apex in a V configuration, said apex adapted to be disposed at the side of the joint toward which flexure is performed.

5. The finger splint of claim 4, wherein said apex is slightly yieldable to alter selectively the angle subtended between said ring members.

6. The finger splint of claim 1, wherein said second ring member is adapted to be fitted about the forward portion of the finger joint with clearance for free flexion of the finger joint.

* * * * *